(12) United States Patent
Askvik et al.

(10) Patent No.: US 12,139,683 B2
(45) Date of Patent: Nov. 12, 2024

(54) METHOD AND SYSTEM FOR COMPRESSING GAS

(71) Applicant: EQUINOR ENERGY AS, Stavanger (NO)

(72) Inventors: Kjell Magne Askvik, Stavanger (NO); Kurt Edal, Stavanger (NO); Jens Grimsgaard, Stavanger (NO); Knut Simon Helland, Stavanger (NO); Jone Torsvik, Søreidgrend (NO); Steinar Wasa Tverlid, Garnes (NO); Marta Vabø, Stavanger (NO)

(73) Assignee: EQUINOR ENERGY AS, Stavanger (NO)

( * ) Notice: Subject to any disclaimer, the term of this patent is extended or adjusted under 35 U.S.C. 154(b) by 267 days.

(21) Appl. No.: 17/785,840

(22) PCT Filed: Dec. 14, 2020

(86) PCT No.: PCT/NO2020/050315
§ 371 (c)(1),
(2) Date: Jun. 15, 2022

(87) PCT Pub. No.: WO2021/125970
PCT Pub. Date: Jun. 24, 2021

(65) Prior Publication Data
US 2023/0086982 A1    Mar. 23, 2023

(30) Foreign Application Priority Data
Dec. 16, 2019    (GB) ...................................... 1918492

(51) Int. Cl.
*B01J 3/00*       (2006.01)
*B01J 19/00*     (2006.01)
(Continued)

(52) U.S. Cl.
CPC ................ *C10L 3/108* (2013.01); *B01J 3/00* (2013.01); *B01J 19/00* (2013.01); *C07C 9/04* (2013.01)

(58) Field of Classification Search
None
See application file for complete search history.

(56) References Cited

U.S. PATENT DOCUMENTS

| | | | |
|---|---|---|---|
| 7,560,028 B1 * | 7/2009 | Simmons | C02F 1/22 62/541 |
| 7,932,423 B2 * | 4/2011 | Shepherd | C10L 3/102 95/199 |

(Continued)

FOREIGN PATENT DOCUMENTS

| | | |
|---|---|---|
| CN | 106753630 A | 5/2017 |
| CN | 103103004 B | 3/2018 |

(Continued)

OTHER PUBLICATIONS

Combined GB Search and Examination Report for GB1918492.8 dated Jun. 4, 2020.

(Continued)

*Primary Examiner* — Tam M Nguyen
(74) *Attorney, Agent, or Firm* — Birch, Stewart, Kolasch & Birch, LLP

(57) ABSTRACT

A hydrocarbon-forming gas compression method comprising: a hydrate formation step in which water and hydrate-forming gas are mixed at a first pressure and a first temperature, resulting in the formation of hydrate; a decomposition step in which the hydrate is warmed, and the hydrate is decomposed to re-generate hydrate-forming gas at a second pressure higher than the first pressure.

7 Claims, 9 Drawing Sheets

(51) Int. Cl.
*C07C 9/04* (2006.01)
*C10L 3/10* (2006.01)

(56) References Cited

U.S. PATENT DOCUMENTS

| | | | |
|---|---|---|---|
| 11,389,766 B2* | 7/2022 | Song | C01B 23/00 |
| 2005/0072301 A1 | 4/2005 | Baciu | |
| 2016/0130517 A1* | 5/2016 | Song | C10L 3/108 585/15 |
| 2016/0184768 A1* | 6/2016 | Bagajewicz | C10L 3/105 95/166 |
| 2018/0002623 A1* | 1/2018 | Noekleby | B01D 19/0036 |
| 2019/0211654 A1 | 7/2019 | Guo | |
| 2019/0211656 A1 | 7/2019 | Chen et al. | |
| 2021/0214626 A1* | 7/2021 | Kezirian | B01J 31/02 |
| 2021/0270117 A1* | 9/2021 | Li | C09K 8/594 |
| 2022/0341440 A1* | 10/2022 | Brenne | F04D 29/705 |

FOREIGN PATENT DOCUMENTS

| | | |
|---|---|---|
| GB | 2540468 A | 1/2017 |
| JP | 2003-322296 A | 11/2003 |
| JP | 2006-160841 A | 6/2006 |
| WO | WO 2019/134220 A1 | 7/2019 |

OTHER PUBLICATIONS

International Search Report for PCT/NO2020/050315 (PCT/ISA/210) mailed on Mar. 4, 2021.
Second GB Examination Report for GB1918492.8 dated Nov. 18, 2021.
Written Opinion of the International Searching Authority for PCT/NO2020/050315 (PCT/ISA/237) mailed on Mar. 4, 2021.

* cited by examiner

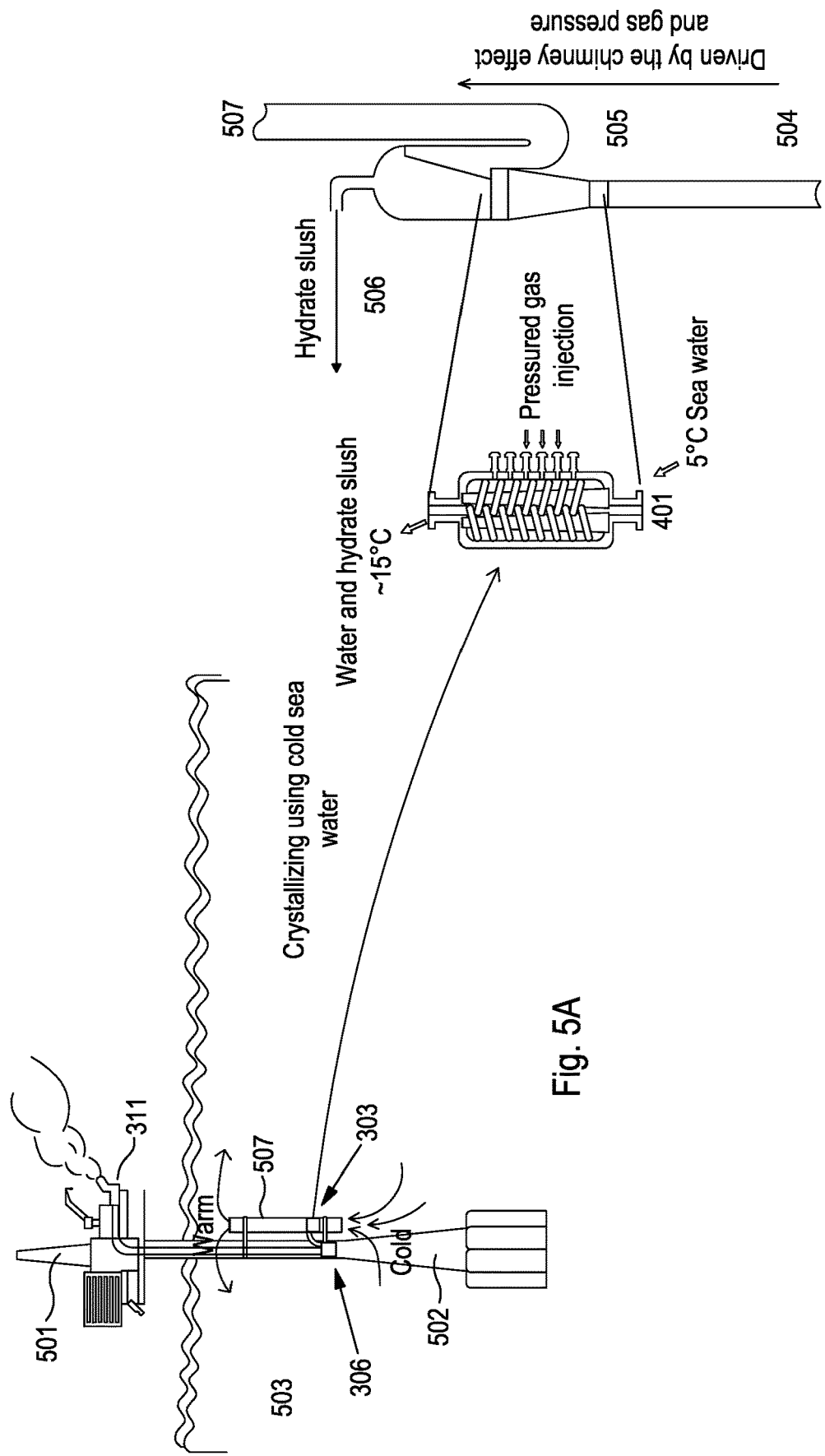

METHOD AND SYSTEM FOR COMPRESSING GAS

FIELD OF THE INVENTION

The present invention relates to systems and methods for compressing gas. In one form the systems compress gas by exploiting temperature and/or pressure differences of liquids and/or gases in a natural environment based on hydrate formation.

BACKGROUND OF THE INVENTION

The term "natural gas" is used here to refer to gas extracted from underground reservoirs, where natural gas is often associated with oil deposits. Natural gas is a combustible mixture of hydrocarbon gases. While it is typically primarily methane, it can also include ethane, propane, butane and pentane. It is well-known to extract natural gas from underground reservoirs, where natural gas is often associated with oil deposits. The reservoirs are frequently located under the sea. When natural gas is extracted its temperature (e.g. 100° C.) is significantly higher than that of the sea and its pressure (e.g. 80 bar) is much higher than atmospheric pressure.

In some wells, the extracted natural gas contains a significant amount of water, which is typically laden with impurities such as salts and minerals. These are removed from the gas in a dehydration/desalting process. Typically some of the gas is inadvertently removed also, and this gas has to be re-pressurized and added back to the natural gas which was not removed. The re-pressurization process is carried out by re-compressors which consume significant energy, which is often supplied by burning fossil fuels.

Once the separation is complete, the natural gas is further compressed by one of more compressor stages to a much higher pressure (such as 200 bar) for transportation to the shore in a pipeline or on a container vessel. A proportion of the natural gas is pressurized to a yet higher pressure (such as 400 bar) by an injection compressor for reinjection into the gas well to increase oil extraction.

Again, both of these processes consume significant energy, which is often supplied by burning fossil fuels.

The process has a number of disadvantages. Firstly, as noted, it consume a large amount of energy. This is particularly true if the system includes drying and cooling units respectively before and after each compressor, as is common. Secondly, due to the fossil fuel which is used to generate the energy, the process generates a large amount of carbon dioxide ($CO_2$) as a by-product. Thirdly, the process is very sensitive to the impurity content of the water contained in the natural gas, and for this reason the machinery which carries out the compression processes is maintenance intensive. For example, a classic gas compressor is composed of heavy rotating equipment which is often sensitive to liquids, which can even be generated during the compression process. If the compression equipment fails, the entire natural gas production process has to be suspended, which is expensive. Furthermore, the compressor equipment has a very high capital cost. Additionally, it has a very high noise profile.

SUMMARY OF THE INVENTION

The present disclosure is concerned with gases of a type which are capable of reacting with water to form hydrates. Such gases are referred to here as "hydrate-forming gases". Examples of hydrate-forming gases include hydrocarbon gases such as methane, ethane, propane, ethylene and acetylene. Accordingly, natural gas is an example of a hydrate-forming gas. Other hydrate-forming gases include hydrogen, fluorocarbons such as HFC and HCFC, as well as carbon dioxide gas ($CO_2$), nitrogen, ammonia, argon (Ar), xenon (Xe) and various other gases.

The invention aims to provide new and useful methods and systems for increasing the pressure of hydrate-forming gas, and to provide uses for the pressurized hydrate-forming gas.

In general terms, the present invention employs a method including:

a hydrate formation step in which water and hydrate-forming gas are mixed at a first pressure, resulting in the formation of hydrate, a decomposition step in which the hydrate is warmed, and the hydrate is decomposed to re-generate hydrate-forming gas at a second pressure higher than the first pressure.

In other words, temperature control is used to produce a heat-cycle in which the pressure of the hydrate-forming gas is increased. In some environments, the temperature control can be effected by making use of natural elements which are at differing respective temperatures, in particular natural gas as it emerges from an oil well, and/or naturally occurring water, such as seawater. Excess heat of a hydrocarbon production facility can be used for the step of warming the hydrate in the decomposition step. Thus, the present invention makes it possible to exploit the difference in temperature of naturally occurring entities to increase the pressure of the hydrate-forming gas.

In a preferred case, the hydrate-forming gas is natural gas which has been extracted from a natural gas reservoir. Optionally, the step of cooling may be performed using ambient water (that is, a natural water source), by exploiting the fact that ambient water is at a lower temperature than the natural gas as it leaves the reservoir.

The first pressure in this case may be a pressure at which natural gas exits the reservoir, or alternatively a slightly reduced pressure due to pressure losses at the well-head. Certain embodiments of the invention make it possible to increase the pressure of the natural gas to a second pressure which is greater than the pressure at which the natural gas exited the reservoir, without a mechanical pressurization stage, by exploiting the temperature difference between the gas exiting the reservoir and the ambient water, or temperature differences using excess heat from a production facility.

The use of hydrate-forming gases which are hydrocarbons is particularly suitable because in this case there is typically a narrow temperature range (such as under 30° wide, or even under 20° wide) such that the minimum pressure at which hydrates are stable varies by at least a factor of 10 (the hydrates of hydrocarbons are typically solids in this temperature range). Thus, controlling the temperature of the gas-water mixture in a narrow temperature range can give dramatic control of the pressure after the hydrates decompose. Furthermore, this temperature range tends to lie within with the range of temperatures which are experienced in the environment of a gas extraction well, where there is typically ambient water (e.g. seawater) with a temperature of no more than 20° C., and frequently about 10° C., while the natural gas itself often exits the reservoir with a temperature at or above 80° C.

The increased pressure of the hydrate-forming gas can be used in multiple ways. In one example, the process of the invention preferably further includes an electrical power generation step in which the hydrate-forming gas is used to drive an electrical generator. In the electrical power generation step, the pressure of the hydrate-forming gas may be reduced to a third pressure which is less than the second pressure, but which is greater than the first pressure.

In particular, in the case that the hydrate-forming gas is natural gas, the third pressure may be a pressure at which it is desirable to pump the natural gas to an on-shore location.

In another example, in the case that the hydrate-forming gas is natural gas, the increased pressure natural gas can be used for any of the purposes for which additionally-compressed natural gas is used in known oil or gas extraction processes, such as transporting the natural gas to shore (along a pipeline, or in a container vehicle), or for injecting material (e.g. water or the hydrate-forming gas itself) into the well to yield further oil extraction. Alternatively, the high pressure natural gas can be stored in containers to be transported to customers. A high pressure gas may also be mixed with a second gas with an initial lower pressure for transporting the mixture to a processing facility.

The ability to use natural gas in this way can dramatically reduce energy consumption at the gas extraction site. In effect, a major power consumption is eliminated, and the use of natural gas in this way can perhaps even turned into a source of power. Due to this change there can be a dramatic reduction in the amount of carbon dioxide generation which is required for natural gas extraction. An underlying reason for reduction in energy consumption is that the gas which is compressed using hydrates does not have a high temperature when compared to gas which is compressed with many conventional means.

Furthermore, since the process reduces or avoids the needs for compressors, it may reduce the maintenance associated with gas compression. Preferred embodiments of the invention may have hardly any moving parts. The moving parts may for example be limited to valves and a low pressure cooling pump. It is expected that embodiments of the invention far less maintenance intensive than existing natural gas pressurization equipment.

Finally, since the need for compressors is reduced or eliminated, the physical space occupied by the natural gas extraction equipment may be reduced. This may result in large cost savings, particularly in the case of extraction systems which are located aboard a floating platform.

In other applications of the invention, the hydrate-forming gas is not a hydrocarbon. It may for example be any one of nitrogen, argon or carbon dioxide. Particularly in this case, embodiments of the invention may transform the hydrate-forming gas in a closed cycle, repeated forming it into hydrates, and then decomposing the hydrates.

Some embodiments of the invention may be used to obtain electrical power using natural sources of media (e.g. water) which are at two different respective temperatures.

Furthermore, some embodiments of the invention may be powered by an external energy source. For example, the external energy source may power a heat pump which drives heat from a first region where hydrates are to form, to a second region where they are to decompose. The pressurized gas may be stored until energy production is desired. In this manner, embodiments of the invention may be used to obtain high-pressure hydrate-forming gas from a varying energy source. The high-pressure hydrate-forming gas can be used to generate electrical power with a different timing from the supply of energy the energy source.

Preferably, the water contains an anti-agglomeration (AA) reagent. Presence of AA will tend to ensure that the hydrates remain as small crystals in a slush type configuration in the water. This may increase the speed of the entire process, because it means that it is less reliant on heat conduction. Furthermore, avoiding formation of large hydrate crystals may reduce mechanical stresses within the system. Instead (or in addition to) using AA one may also use mechanical mixing or stirring such that the crystals remain small.

The term "mixture" is used here to mean that the water and hydrate-forming gas are at least in contact with each other in a single chamber. In many cases the gas will lie as a separate layer over the water in the mixture.

BRIEF DESCRIPTION OF THE DRAWINGS

Embodiments of the invention will now be described for the sake of example only with reference to the following figures, in which:

FIG. 5 illustrates schematically an implementation of the systems of FIGS. 3 and 4;

DETAILED DESCRIPTION OF THE DRAWINGS

Figure 1:
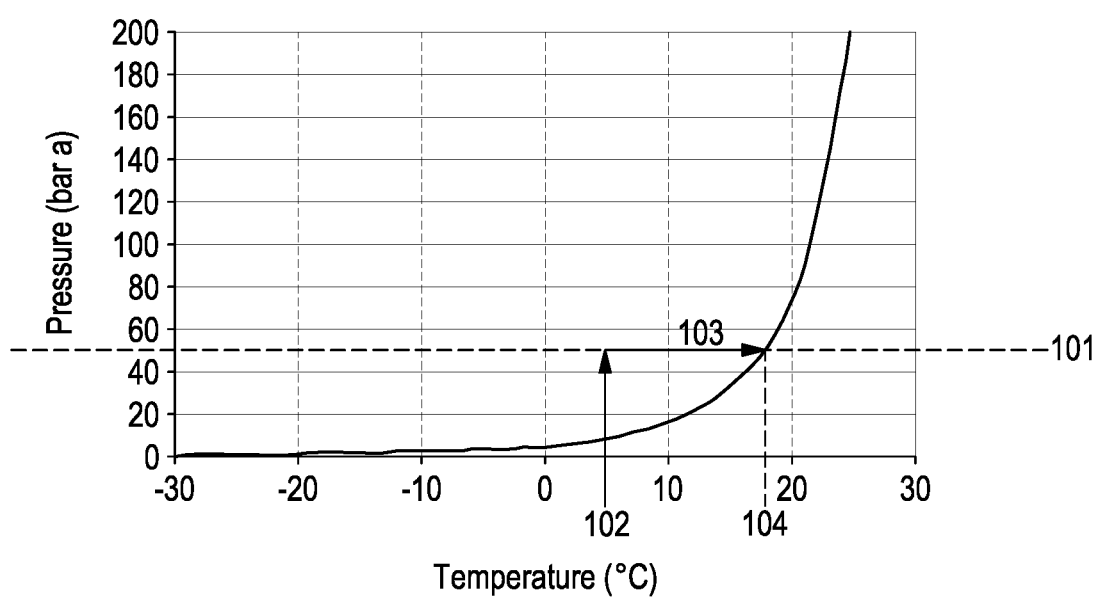
FIG. 1 is a known pressure-temperature phase diagram indicating the range of temperature and pressure at which stable hydrates are formed.

FIG. 1 is a phase diagram illustrating phase transitions which occur in a mixture of water with a hydrate-forming gas. The area of the diagram above the graph corresponds to stable hydrates, while the area below the graph corresponds to separate gas and water phases. The specific hydrate-forming gas which was used to generate FIG. 1 has the composition:

$N_2$: 2%
$CO_2$: 2%
Methane (C1) 63.6%
Ethane (C2): 10.9%
Proplene (C3): 9.8%
i-Butane (i-C4): 1.3%
n-Butane (n-C4): 3.9%
i-Pentane (i-C5): 1.1%
n-Pentane (n-C5): 1.7% which is a typical natural gas composition. Although the exact form of FIG. 1 varies depending on the gas composition, the general shape of the graph remains the same. In particular it will be observed that for a relatively small temperature range (10° C. to 25° C.) the pressure below which hydrates are stable increases remarkably, from under 20 bars to over 200 bars.

Dotted line 101 indicates a 50 bara pressure as an exemplary pressure of hydrocarbons when emerging from a well. Arrow 102 indicates a possible temperature of 5° C. near the seabed or deep below the water surface. Arrow 103 shows the path of heating up the stable hydrates at a 50 bara pressure from a temperature of 5° C. to 18° C., and at those conditions (50 bara and 18° C.) a phase transition to gas and water will occur. If the hydrates are placed in a confined space, the pressure will rise when more hydrates are melting, and the state moves along the curve upwards until all hydrates are melted, at an exemplary pressure of around 1000 bara.

A 50 bara pressure is mentioned as an exemplary pressure of hydrocarbons emerging from a well. In a practical implementation of the concept disclosed herein, a conventional choke may be omitted in order to make use of the well pressure. A choke is a conventional valve used to regulate or reduce pressure of hydrocarbons emerging from a well.

Figure 2:
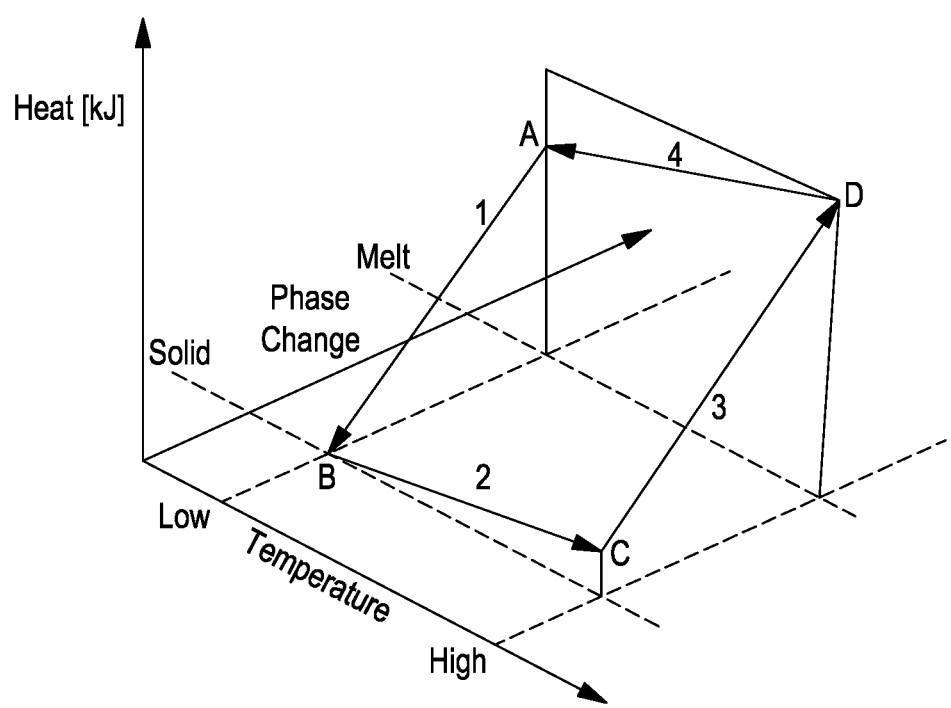
FIG. 2 is a known diagram illustration the energy content of a mixture of water and a hydrate-forming gas during a reversible phase transition.

FIG. 2 shows schematically the four transitions which occur during a reversible process of hydrate formation and decomposition employed in the embodiments of the invention described below. A first horizontal axis of the diagram represents temperature. The vertical axis represents the energy which is contained in a mixture of water and hydrate-forming gas during the process. The second horizontal axis illustrates schematically the state of the mixture, i.e. the phase change between solid state (i.e. hydrates have been formed) and melted state (i.e. the hydrates have decomposed).

Consider for example, the state marked A as a starting state. In this state, the water and hydrate-forming gas are present together in a chamber (typically with the gas in a layer above the water), and the temperature and pressure of the system are slightly below a phase transition temperature. Accordingly the state A is unstable, and a transition occurs (a process marked as 1), in which hydrate crystals are formed. Significant energy is expelled in this process, and this energy must be removed from the system for process 1 to be completed, resulting in hydrate crystals in state B. In process 2, the hydrate crystals are very slightly heated to a temperature above the phase transition temperature (a process marked as 2), where again the hydrates (now in state C) are unstable. In process 3, the hydrate crystals melt, regenerating the hydrate-forming gas and separately the water. Significant energy must be input to the system during process 3, resulting in decomposed gas and water (state D). Finally, slight cooling of the system returns the mixture to state A (process 4).

Note that the small amounts of energy respectively absorbed and released in processes 2 and 4 cancel each other, as do the much larger amounts of energy respectively released and absorbed in processes 1 and 3. Processes 1 and 3 typically require a heat pump, and/or external warm and cool media which the gas-water mixture can exchange heat with. The heat exchange with an external supply of energy amounts to energy consumed to the system to achieve the gas compression.

Figure 3:
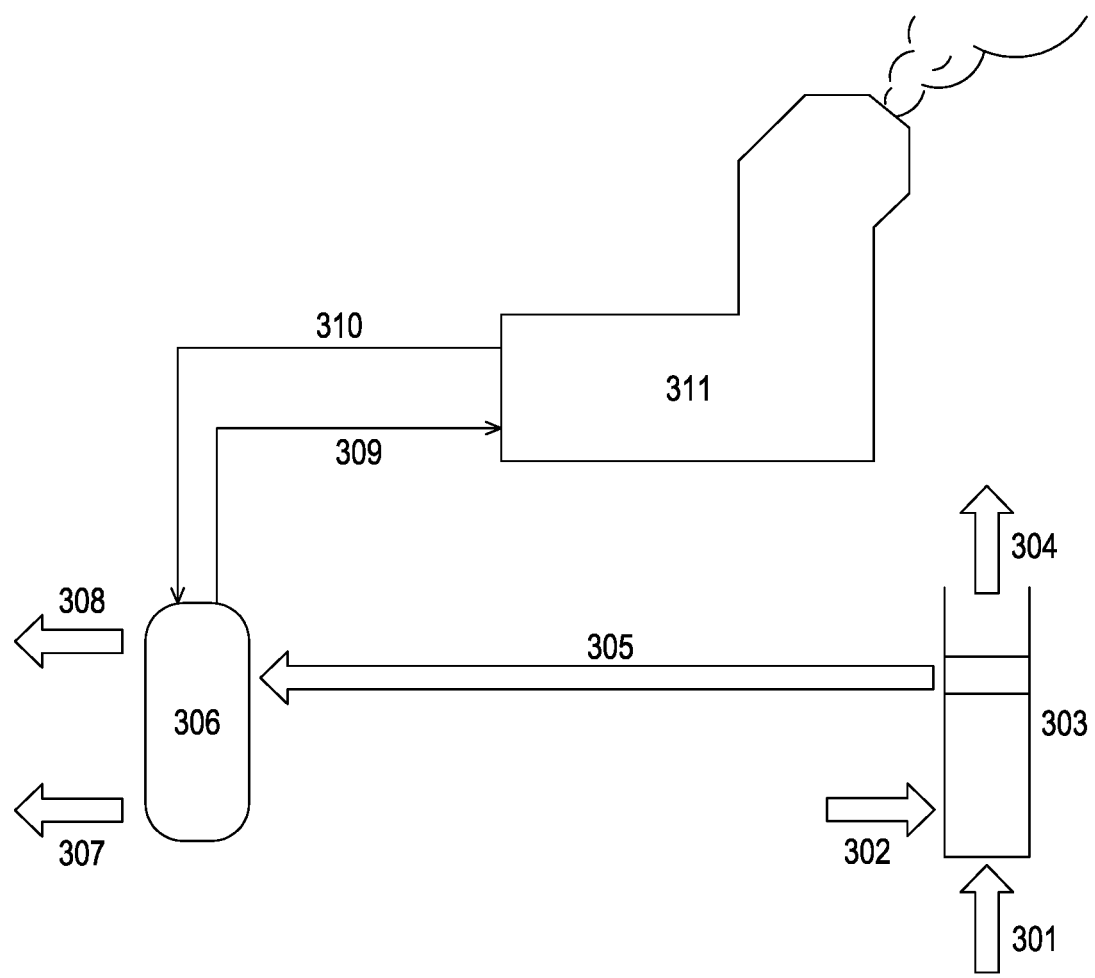
FIG. 3 illustrates schematically and in cross-section a system which can be used in an embodiment of the invention.

Referring to FIG. 3 a system is illustrated schematically which can be used for compressing gas based on a hydrate cycle under the influence of temperature differences occurring in existing offshore production platforms. Starting from the right-hand side of the schematic drawing, seawater 301 and hydrate-forming gas 302 are mixed together in a mixing device 303. The seawater is taken in from the surrounding sea (which may also be an ocean, lake or other volume of water) and the gas 302 may be taken from a hydrocarbon producing well. Only part of the seawater 301 forms hydrates and the remaining part of the seawater 304 is released again into the surrounding sea. The temperature of the released seawater is higher than the seawater taken into the mixing device because the hydrate formation process releases energy, as described in connection with FIG. 2 when moving from state A to state B. The salt content of the released seawater is also higher because the hydrate formation process uses only water molecules. Hydrates 305 are produced and transported to compressing device 307. The mixing device 303 will be described in more detail below with reference to FIG. 4.

The produced hydrates 305 are transported to tank 306, which will also be described in more detail below. The step of transporting hydrates provides a technical advantage over transporting gas, which would need to be compressed at this stage. The distance between elements 303 and 306 may be short, for example 1m, or may be long, as long as 100 km. At tank 306, the hydrates are heated to regenerate the hydrate-forming gas and separately the water, described as process 3 in connection with FIG. 2 in which state C transforms to state D. Water 307 and high pressure gas 308 are extracted. The water 307 can be released into the sea, while the pressurised gas can, for example, be stored in containers to be transported to consumers.

The inventors have realised that excess energy of the existing hydrocarbon producing facility can be used for the energy required to cause the phase transition from hydrates to gas. Temperature differences exist within the sea between the temperature at the seabed and the temperature below the waves.

Well fluids have typically also a higher temperature than seawater, which provides another temperature differential which could be used to cause a phase transition. However, there are also other opportunities to re-use excess energy at a facility such as a production platform which includes a variety of heavy machinery. One specific example of excess heat is a chimney for releasing gases from a burning process. FIG. 3 illustrates chimney 311 and a circuit including incoming cold water through a line 309 and a return line 310 with outgoing hot water or steam. The circuit may be closed or open. The water or other fluid in the circuit is used for transporting heat to tank 306.

A realistic numerical example of a process such as illustrated in FIG. 3 is as follows: 43 m$^3$/min of seawater 301 enters mixing device 303 together with 1000 m$^3$/min of gas 302. At 304, 38.9 m$^3$/min of sea water is released again, also releasing 39.7 MW of energy. At 305, 5.9 m$^3$/min of hydrates are transported to tank 306. Around 500 kg/min of water is pumped around the circuit 309 and 310 to transport 40.1 MW of energy from the chimney towards tank 306. The amount of released water at 307 is 4.7 m$^3$/min and 1000 m$^3$/min of compressed gas, at a pressure of 1000 bara, is released at 308. This specific example is not intended as a limiting example, and a range of other numerical examples can be used while achieving the same technical effect of providing compressed gas.

Figure 4:
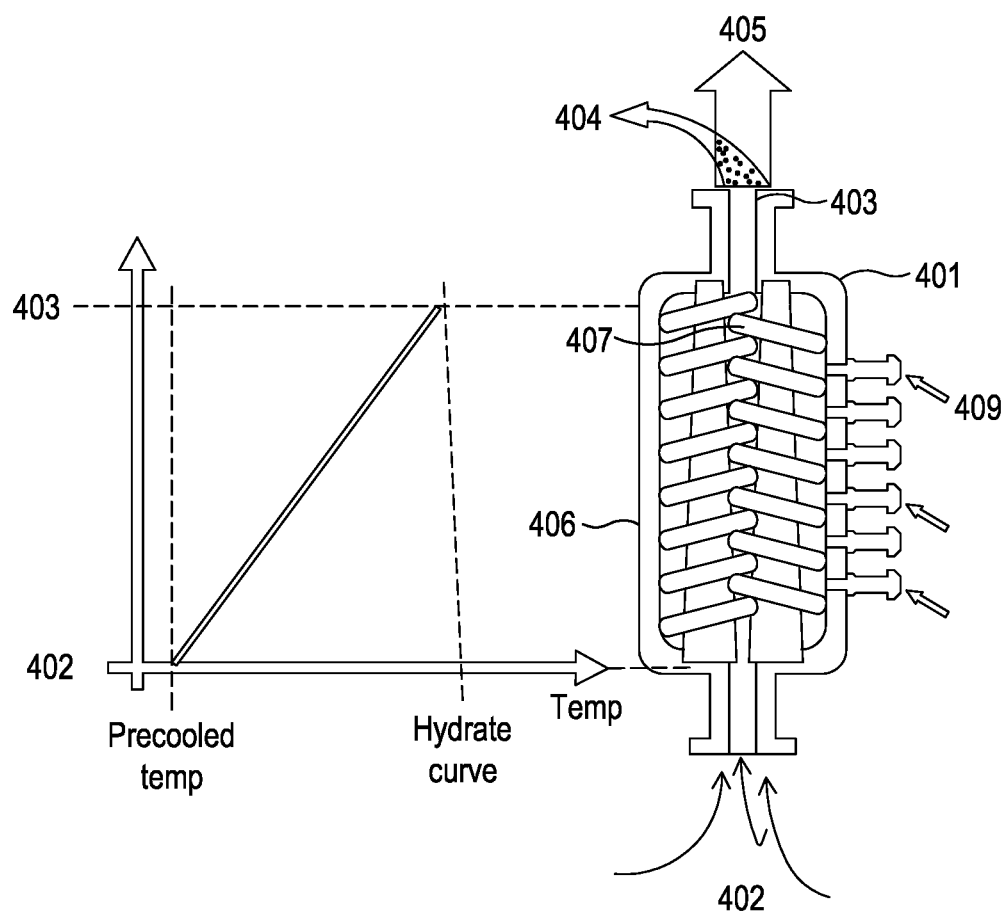
FIG. 4 illustrates schematically a first embodiment of a mixing device as shown in FIG. 3.

FIG. 4 illustrates a specific example 401 of mixing device 303. The device has an input 402 for seawater and an output 403 for letting out hydrates (around 10% of the output) and remaining seawater 405 which is released back into the sea as described before. The device comprises a housing 406 to contain a corresponding set of two screws 407, whereby the housing and the screw define recesses for receiving pressured gas 408 through inputs 409. The volume within the expander for receiving gas and hydrates increases towards the top of the device while the two screws turn. The expander is known as such to the skilled person, and can also be run in reverse to act as a compressor for different purposes. Some of the energy of the injected gas may also be used for making the screws turn.

FIG. 5A illustrates a possible practical implementation of the devices disclosed herein, whereby a production platform 501 placed on a leg 502 is set in the sea (or ocean) 503. The parts corresponding to those discussed in connection with FIG. 3 are indicated with corresponding reference numbers: mixing device 303, tank 306, chimney 311, while the connecting conduits are illustrated but not numbered again. The mixing device 303 is set against leg 502 at sufficient depth for intake of cold seawater. Mixing device 303 is embodied by screw expander 401 shown again in FIG. 5B.

FIG. 5C illustrates the screw expander connected to an inlet pipe 504 which takes in the cold seawater. The outlet of the expander contains a mixture of hydrate slush and water, and an outlet pipe is used in the illustrated example which has an S-bend 505. The S-bend works in a manner similar to an air-lock in a kitchen sink, whereby the lighter hydrate slush exits through outlet 506 before the S-bend, while the heavier water is driven through the S-bend and continues in outlet pipe 507. As mentioned before the water in the outlet has a higher temperature and as shown in FIG. 5A a relatively long outlet pipe 507 is used to transport the warmer outlet water away from the mixing device by way of a chimney effect within pipe 507. Other devices for separating lighter hydrates from heavier seawater may be used, such as a centrifugal separator.

Figure 6B:
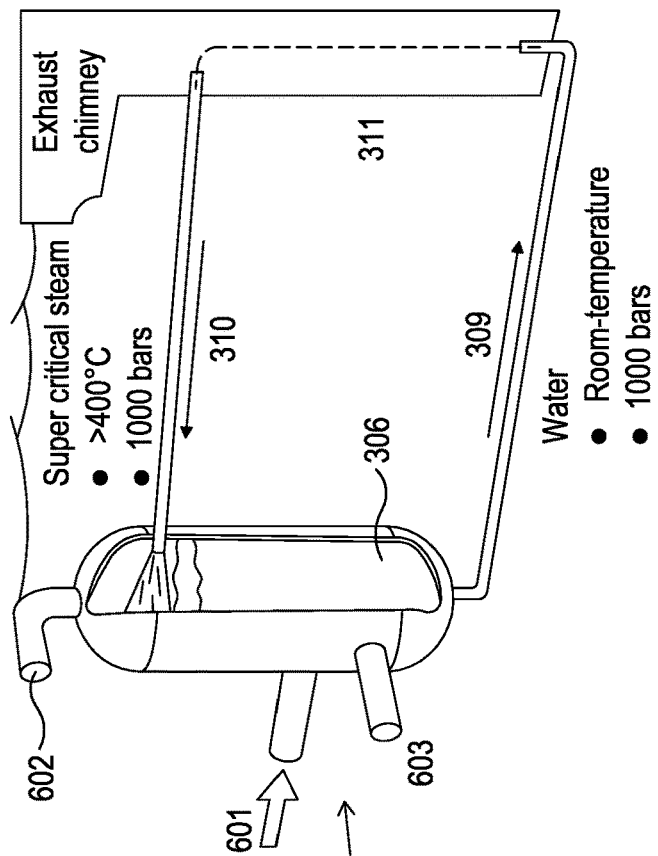
FIG. 6 illustrates schematically a further embodiment of the invention.
Figure 6A:
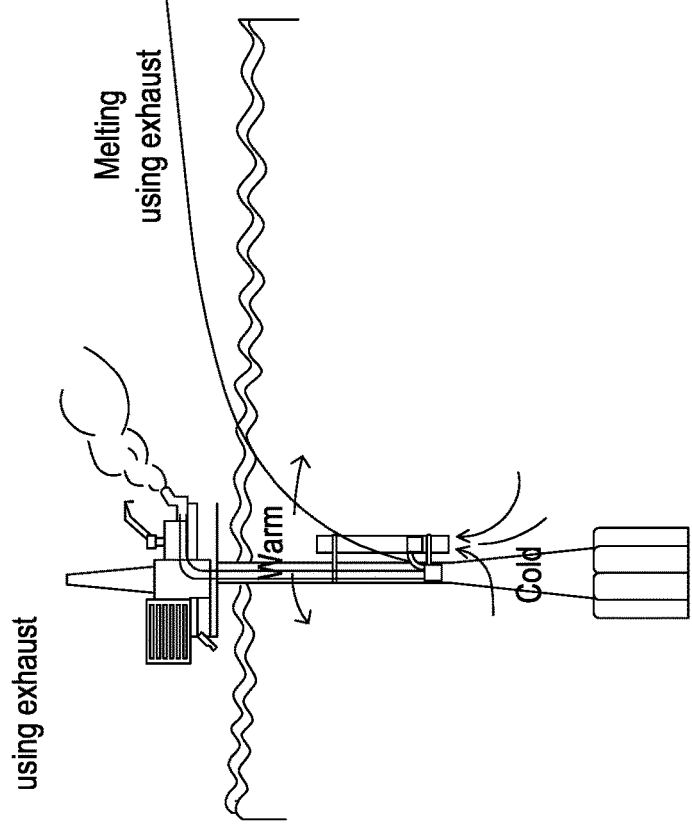

FIG. 6 illustrates tank 306 in more detail when used in the implementation illustrated in FIG. 6A as discussed before. The tank 306 has an inlet 601 for receiving the hydrates produced as described before. The tank further has an outlet 602 for letting out the pressurised gas, whereby the outlet 602 is provided at a top or at least near a higher part of the tank to take advantage of the lighter gas rising to the top of the tank. A further outlet 603 is provided to let out the water. The water is also pressurised and can be used for a specific purpose such as injection into the well, or can simply be released into the sea. The rate of releasing gas into the sea needs to be controlled carefully such that the gas is absorbed, whereby the rate of absorption depends on the temperature. Channels 309 and 310 of the water heating circuit are illustrated as leading the water past chimney 311. The inlet water 309 may be around 1000 bara at room temperature, while the returning steam may be at the same pressure, but below or above a super-critical state at a temperature at or over 400° C. The inlet water may be taken from a lower part of the tank 306, while the steam is injected at a top part of the tank. As illustrated, a preferred embodiment is the channels 309 and 310 being in open connection to the tank 306, but in an alternative embodiment the channels may form a closed circuit which is in temperature communication with the tank to exchange heat without releasing or taking out water from the tank. The tank further includes valves for pressure control, as described in more detail below in connection with FIGS. 7 and 8.

An example of efficiency achieved with the illustrated setup is a temperature difference of 445° C. between the cold 5° C. and steam of 450° C., an energy delivery of 25 MW, an energy exhaust of 19 MW.

Figure 7:
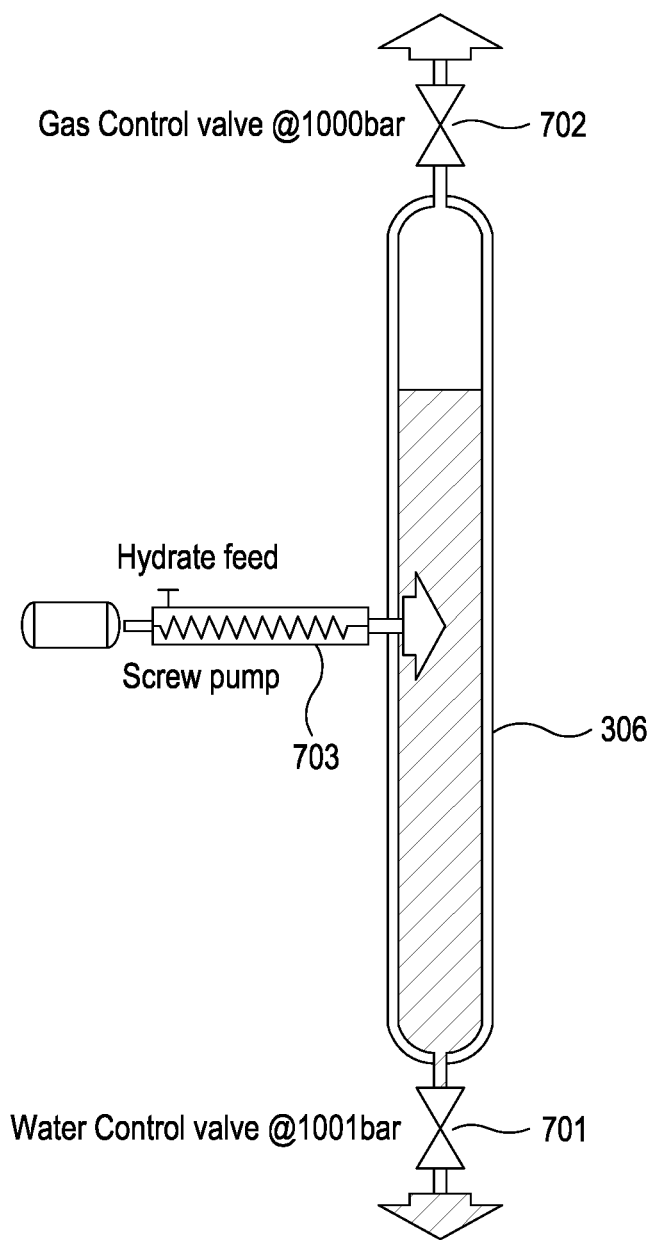
FIG. 7 illustrates schematically an embodiment of a tank.

FIG. 7 illustrates one optional arrangement of valves for controlling the pressure within tank 306. The gas outlet is controlled with a control valve 702, while the water outlet is controlled with control valve 701. The inlet of hydrates is regulated with a screw pump 703. The method of operating this tank is as follows: first hydrates are fed into the tank by rotating the screw of the screw pump; then the tank is closed and heat circulation is started to melt the hydrates and consequently the pressure will increase. When the pressure reaches a threshold pressure at which the gas control valve opens, the gas will flow into a container which is attached to the outlet. When the gas is let out, the water level will increase and when the pressure of the water column reaches a threshold pressure of the water control valve 701, water is released. This process can run continuously during production.

Figure 8A:
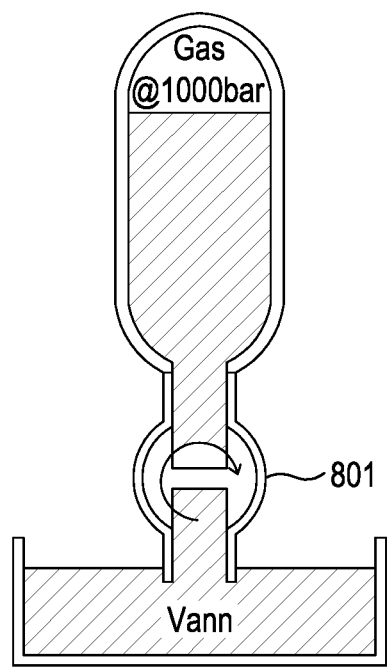
FIG. 8 illustrates schematically another embodiment of a tank.
Figure 8B:
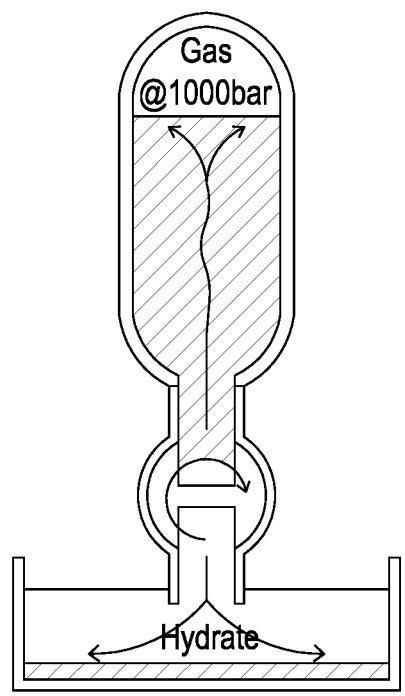

FIG. 8 illustrates alternative embodiments for managing the pressure in tank 306 including a rotatable sluice. The sluice is rotatable around an axis and has one or more outward facing chambers which can be filled up with a liquid or gas when they face an opening, but retain the fluid or gas (as well as the fluid or gas pressure) when facing away from an opening during rotation of the sluice. One opening faces the tank while another opening faces an outlet, so the chamber alternatingly faces the tank and the outlet. In FIG. 8A, a rotating valve 801 is provided at a lower end to act as the sluice for removing and replacing water from the tank 306, without significantly changing the pressure in the tank. Rotating the sluice does not require a large amount of energy. In FIG. B, hydrates are provided at an outlet of the rotating valve, such that when the valves rotates, water is let out while hydrates are let in. The use of a sluice has the technical advantage of increasing the efficiency of the system because rotating the sluice valve does not consume much energy when compared to screw pump 703 of FIG. 7. A valve may be provided at the top of the tank to remove compressed gas to a container or pipe for transporting the compressed gas away from the system.

Figure 9:
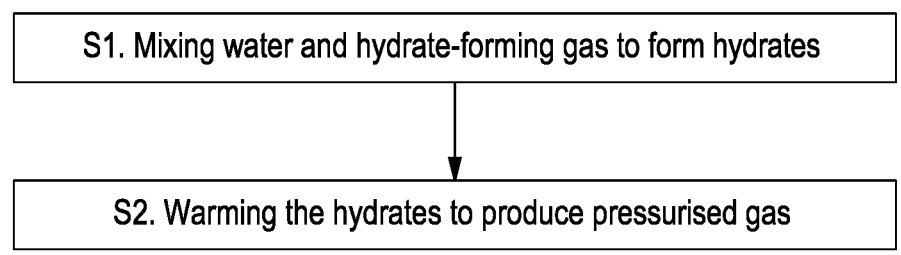
FIG. 9 is a flow diagram.

FIG. 9 is a flow diagram illustrating the two main steps of the method disclosed herein, comprising (S1) mixing water and hydrate-forming gas to form hydrates and (S2) warming the hydrates in a confined space to produce pressurised gas. Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A hydrocarbon-forming gas compression system comprising:
   a mixing device comprising an inlet for hydrocarbon-forming gas, an inlet for water, an outlet for water and an outlet for hydrates;
   a tank comprising an inlet for hydrates communicatively coupled to said outlet for hydrates from the mixing device, an outlet for compressed gas, an outlet for water; and
   a heat exchanging system for heating the tank.

2. The system according to claim 1, wherein the heat exchanging system comprises a circuit, the circuit comprising a water transport pipe to a heat source and a return pipe for transporting water or steam with a higher temperature than the water in the water transport pipe to the tank.

3. The system according to claim 1, wherein the tank and the mixing device are attached to a leg of a production platform and wherein the inlet for water is communicatively coupled to the surrounding seawater.

4. The system according to claim 1 further including a discharge mechanism for discharging fluid in the tank.

5. The system according to claim 1, wherein the mixing device comprises a screw expander.

6. The system according to claim 1, wherein the tank comprises a plurality of pressure control valves.

7. The system according to claim 1, wherein the tank comprises a sluice valve.

* * * * *